(12) United States Patent
Qiu et al.

US009028727B2

(10) Patent No.: US 9,028,727 B2
(45) Date of Patent: May 12, 2015

(54) DIELECTRIC FLUIDS COMPRISING POLYOL ESTERS

(75) Inventors: Weiming Qiu, Wilmington, DE (US); Peter A Brown, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 392 days.

(21) Appl. No.: 13/594,011

(22) Filed: Aug. 24, 2012

(65) Prior Publication Data

US 2013/0225023 A1 Aug. 29, 2013

Related U.S. Application Data

(60) Provisional application No. 61/538,318, filed on Sep. 23, 2011, provisional application No. 61/538,303, filed on Sep. 23, 2011, provisional application No. 61/538,298, filed on Sep. 23, 2011, provisional application No. 61/560,840, filed on Nov. 17, 2011, provisional application No. 61/560,845, filed on Nov. 17, 2011, provisional application No. 61/560,850, filed on Nov. 17, 2011.

(51) Int. Cl.
| | |
|---|---|
| *H01B 3/20* | (2006.01) |
| *C07C 67/29* | (2006.01) |
| *C09K 5/06* | (2006.01) |
| *C07C 69/58* | (2006.01) |

(52) U.S. Cl.
CPC .... *H01B 3/20* (2013.01); *C07C 67/29* (2013.01); *C09K 5/063* (2013.01); *C07C 69/58* (2013.01)

(58) Field of Classification Search
None
See application file for complete search history.

(56) References Cited

U.S. PATENT DOCUMENTS

| | | | |
|---|---|---|---|
| 3,894,959 A | 7/1975 | Gardiner et al. |
| 4,627,192 A | 12/1986 | Fick |
| 4,812,262 A | 3/1989 | Shinzawa et al. |
| 4,868,329 A | 9/1989 | Powanda et al. |
| 5,736,915 A | 4/1998 | Goedde et al. |
| 5,767,338 A | 6/1998 | Fan et al. |
| 5,861,187 A | 1/1999 | Debonte et al. |
| 5,981,781 A | 11/1999 | Knowlton |
| 6,037,537 A | 3/2000 | McShane et al. |
| 6,051,539 A | 4/2000 | Kodali et al. |
| 6,160,144 A | 12/2000 | Bongardt et al. |
| 6,278,006 B1 | 8/2001 | Kodali et al. |
| 6,291,409 B1 | 9/2001 | Kodali et al. |
| 6,398,986 B1 | 6/2002 | McShane et al. |
| 6,410,492 B1 | 6/2002 | Shimomura et al. |
| 6,465,401 B1 | 10/2002 | Kodali et al. |
| 6,689,722 B1 | 2/2004 | Holst-Grubbe et al. |
| 6,726,857 B2 | 4/2004 | Goedde et al. |
| 6,905,638 B2 | 6/2005 | Corkran et al. |
| 6,943,262 B2 | 9/2005 | Kodali et al. |
| 7,048,875 B2 | 5/2006 | Oommen et al. |
| 7,220,710 B2 | 5/2007 | Kunz et al. |
| 7,252,779 B2 | 8/2007 | Mosier et al. |
| 7,476,344 B2 | 1/2009 | Sunkara et al. |
| 7,514,394 B2 | 4/2009 | Kodali et al. |
| 7,524,440 B2 | 4/2009 | Rapp et al. |
| 7,815,821 B2 | 10/2010 | Rapp et al. |
| 7,833,440 B2 | 11/2010 | Bessede et al. |
| 7,871,546 B2 | 1/2011 | Corkran et al. |
| 2003/0124941 A1 | 7/2003 | Hwo et al. |
| 2003/0186824 A1 | 10/2003 | Chiu et al. |
| 2005/0040375 A1 | 2/2005 | Corkran et al. |
| 2008/0033201 A1 | 2/2008 | Hof et al. |
| 2010/0151112 A1 | 6/2010 | Franklin et al. |
| 2010/0243969 A1 * | 9/2010 | Rebouillat et al. ............ 252/579 |
| 2010/0303957 A1 | 12/2010 | Brooks et al. |
| 2011/0012071 A1 | 1/2011 | Rapp et al. |
| 2011/0316660 A1 | 12/2011 | Levit et al. |
| 2012/0156461 A1 | 6/2012 | Krishnamurthy |

FOREIGN PATENT DOCUMENTS

| | | |
|---|---|---|
| CA | 1326683 C | 2/1994 |
| CA | 2492565 A1 | 7/2006 |
| CA | 2594765 A1 | 7/2006 |
| WO | 94/11516 A1 | 5/1994 |
| WO | 2004108871 A2 | 12/2004 |
| WO | 2006074553 A1 | 7/2006 |
| WO | 2010097358 A1 | 9/2010 |
| WO | 2010111698 A2 | 9/2010 |
| WO | 2010151548 A1 | 12/2010 |

OTHER PUBLICATIONS

International Search Report dated Nov. 2, 2012, PCT/US2012/052361.
International Search Report dated Feb. 15, 2013, PCT/US2012/052290.
Co-pending application CL5235 USNP published as US 2013-0337249 A1, filed Aug. 24, 2012.
Midel® 7131 Safety Data Sheet (Dec. 2010).
Cooper Power Systems Envirotemp FR3 Fluid technical bulletin (Apr. 2010).
Environmental Technology Verification Report, Cooper Power Systems Envirotemp(R) FR3(TM) Vegetable Oil-Based Insulating Dielectric Fluid, May 2002, DTSC R-02-02, EPA 600/R-02/042.
Environmental Technoloay Verification Report, ABB Inc, BIOTEMP(R) Vegetable Oil-Based Insulating Dielectric Fluid, Jun. 2002, DTSC R-02-03, EPA 600/R-02/043.
Ulf Schuchardt, Rocardo Sercheli, Rogerio Matheus Vargas, "Transesterification of Vegetable Oils, a Review" J. Braz. Chem Soc, vol. 9, No. 1, 199-210, 1998.

* cited by examiner

*Primary Examiner* — Necholus Ogden, Jr.

(57) ABSTRACT

Dielectric fluids are provided, the dielectric fluids comprising a mixture of polyol esters derived from a reaction of a) a polyol comprising pentaerythritol, trimethylolpropane, neopentyl glycol, or combinations thereof, and b) a mixture of fatty acid esters derived from a high oleic soybean oil comprising fatty acid moieties, wherein the high oleic soybean oil has a C18:1 content of greater than 65% of the fatty acid moieties in the oil, and a combined C18:2 and C18:3 content of less than 20% of the fatty acid moieties in the oil. Also provided are electrical apparatuses comprising the dielectric fluids, and processes for preparing the mixtures of polyol esters.

18 Claims, No Drawings

DIELECTRIC FLUIDS COMPRISING POLYOL ESTERS

This application claims benefit of priority from U.S. Provisional Application No. 61/538,318, filed Sep. 23, 2011; U.S. Provisional Application No. 61/538,303, filed Sep. 23, 2011; U.S. Provisional Application No. 61/538,298, filed Sep. 23, 2011; U.S. Provisional Application No. 61/560,840, filed Nov. 17, 2011; U.S. Provisional Application No. 61/560,845, filed Nov. 17, 2011; and U.S. Provisional Application No. 61/560,850, filed Nov. 17, 2011, all of which are incorporated by reference in their entirety.

FIELD OF THE INVENTION

Dielectric fluids comprising a mixture of polyol esters are provided, as are processes for preparing the mixtures of polyol esters, and electrical apparatuses comprising the dielectric fluids.

BACKGROUND

The electrical industry uses a variety of dielectric fluids which are easily available and generally cost effective. Examples are mineral oil, silicone fluid, and synthetic hydrocarbon oils used in transformers, power cables and capacitors. Such fluids must be electrically insulating, resistant to degradation, and be able to act as a heat transfer medium so that heat generated in an electrical apparatus can be dissipated to the surrounding environment.

However, currently used fluids also have several deficiencies. Many of these fluids are not considered to be biodegradable in a reasonable time frame. Some have electrical properties which render them less than optimal. In recent years regulatory agencies have become increasingly concerned about oil spills which can contaminate the ground soil and other areas. A biodegradable dielectric fluid would be desirable for electrical apparatus such as transformers used in populated or ecologically sensitive areas.

U.S. Pat. No. 6,160,144 relates to synthetic esters of alcohols and fatty acid mixtures containing at least 85% by weight of oleic acid and 0.5 to 2.5% by weight of stearic acid and to their use as lubricants and hydraulic oils and for cosmetic purposes.

U.S. Pat. No. 6,278,006 discloses oils containing a triacylglycerol polyol ester and a non-glycerol polyol ester, as well as methods of making such oils and methods for improving lubrication properties of a vegetable oil.

U.S. Pat. No. 7,048,875 relates to a high oleic oil composition useful as an electrical insulation fluid, to electrical insulation fluid compositions, and electrical apparatuses which comprise the same. Disclosed are the electrical properties of high oleic acid triglyceride compositions that comprise fatty acid components of at least 75% oleic acid, less than 10% diunsaturated fatty acid component; less than 3% triunsaturated fatty acid component; and less than 8% saturated fatty acid component. In some preferred embodiments, the electrical insulation fluid comprises fatty acid components of: at least 75% oleic acid, less than 10% linoleic acid, less than 3% linolenic acid, less than 4% stearic acid, and less than 4% palmitic acid.

Published Canadian Patent Application CA 2,492,565 discloses a dielectric coolant having at least a pour point of about −40° C. and comprising a mixture of more than one polyol ester of specified chemical structures, wherein the alkyl groups have chain lengths of $C_5$ to $C_{22}$. Neopentyl glycol and trimethylolpropane are disclosed as preferred polyols.

There is a continuing need for biodegradable dielectric fluids having good oxidative stability. There is an ongoing need for electrical apparatuses which comprise a biodegradable dielectric fluid having good oxidative stability. There is a need for a process to prepare biodegradable dielectric fluids having good oxidative stability.

SUMMARY

Described herein are dielectric fluids comprising a mixture of polyol esters derived from the reaction of a polyol with a mixture of fatty acid esters derived from a high oleic soybean oil. The high oleic soybean oil has a C18:1 content of greater than 65% of the fatty acid moieties in the oil; and a combined C18:2 and C18:3 content of less than 20% of the fatty acid moieties in the oil. The mixtures of polyol esters have electrical properties which make them well suited as insulation fluids in electrical apparatuses. Also described herein are electrical apparatuses comprising the dielectric fluids, a dielectric material impregnated with the dielectric fluid, and processes for making the mixtures of polyol esters of which the dielectric fluids are comprised.

In one embodiment a dielectric fluid is described, wherein the dielectric fluid is a mixture comprising polyol esters derived from a reaction of:

a) a polyol comprising pentaerythritol, trimethylolpropane, neopentyl glycol, or combinations thereof; and b) a mixture of fatty acid esters derived from a high oleic soybean oil comprising fatty acid moieties, wherein the high oleic soybean oil has i) a C18:1 content of greater than 65% of the fatty acid moieties in the oil; and ii) a combined C18:2 and C18:3 content of less than 20% of the fatty acid moieties in the oil.

In one embodiment, the dielectric fluid meets the criteria for "Ready Biodegradation" under the conditions of the 28-day $CO_2$ Evolution Test according to OECD Guideline 301B.

In one embodiment, a process for preparing a mixture of polyol esters is described, the process comprising the steps of a) providing a high oleic soybean oil comprising fatty acid moieties wherein the soybean oil comprises i) a C18:1 content of greater than 65% of the fatty acid moieties in the oil; and ii) a combined C18:2 and C18:3 content of less than 20% of the fatty acid moieties in the oil;

b) reacting the high oleic soybean oil with an aliphatic monoalcohol having a chain length of from 1 to 5 carbons in the presence of a first base catalyst to produce a reaction mixture comprising glycerol and a mixture of fatty acid esters;

c) removing the glycerol; and d) reacting the mixture of fatty acid esters with a polyol comprising pentaerythritol, trimethylolpropane, neopentyl glycol, or combinations thereof in the presence of a second base catalyst to produce a mixture of polyol esters.

In one embodiment an electrical apparatus is described, the electrical apparatus comprising a dielectric fluid wherein the dielectric fluid comprises a mixture comprising polyol esters derived from a reaction of:

a) a polyol comprising pentaerythritol, trimethylolpropane, neopentyl glycol, or combinations thereof; and b) a mixture of fatty acid esters derived from a high oleic soybean oil comprising fatty acid moieties, wherein the high oleic soybean oil has
   i) a C18:1 content of greater than 65% of the fatty acid moieties in the oil; and
   ii) a combined C18:2 and C18:3 content of less than 20% of the fatty acid moieties in the oil.

In one embodiment a dielectric material is described, the dielectric material comprising a cellulosic paper, a synthetic paper, or a nonwoven web; and the dielectric fluid comprising a mixture comprising polyol esters derived from a reaction of:
a) a polyol comprising pentaerythritol, trimethylolpropane, neopentyl glycol, or combinations thereof; and
b) a mixture of fatty acid esters derived from a high oleic soybean oil comprising fatty acid moieties, wherein the high oleic soybean oil has
   i) a C18:1 content of greater than 65% of the fatty acid moieties in the oil; and
   ii) a combined C18:2 and C18:3 content of less than 20% of the fatty acid moieties in the oil.

DETAILED DESCRIPTION OF THE INVENTION

The methods, compositions, and articles described herein are described with reference to the following terms.

As used herein, where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus.

As used herein, the term "wt %" means weight percent.

According to the present invention, high oleic acid content soybean oils are used as starting materials for the production of mixtures of polyol esters. The polyol ester mixtures have physical properties useful for electrical insulation fluids, also referred to as dielectric fluids. Disclosed herein are mixtures of polyol esters having specific structural and physical characteristics and properties, methods of making such mixtures, dielectric fluids which comprise the mixtures of polyol esters, and electrical apparatuses which comprise the dielectric fluids.

Vegetable oils usually have a high percentage of triglyceride esters of saturated and unsaturated organic acids. Oleic acid is a monounsaturated acid found as triglyceride ester in many natural oils including sunflower, olive oil, safflower, canola oil, and soybean oil. High oleic soybean (HOS) oil may be derived from high oleic soybean seeds which have been genetically modified to yield high oleic content, as disclosed in World Patent Publication WO 94/11516, which is hereby incorporated in its entirety by reference. A high oleic soybean seed is a soybean seed wherein oleic acid accounts for greater than 65 percent of the fatty acid moieties in the oil and, preferably, greater than 75 percent of the fatty acid moieties in the oil. High oleic soybean oil may be derived from high oleic soybean seeds as disclosed in U.S. Pat. No. 5,981,781, which is hereby incorporated in its entirety by reference. High oleic soybean oil may be purified by such process steps as refining, bleaching, and deodorizing, as described in U.S. Pat. No. 5,981,781, to obtain refined, bleached, and deodorized high oleic soybean oil (RBD HOS oil). HOS Oil and/or RBD HOS oil may be used in the processes disclosed herein to prepare dielectric fluids comprising a mixture of polyol esters. In one embodiment, HOS oil may comprise refined, bleached, and deodorized high oleic soybean oil.

A triglyceride composition is a glycerol backbone linked to three fatty acid molecules. Pure vegetable oils are triglycerides of certain fatty acids with a carbon chain generally ranging from 16 to 22 carbon atoms, although small amounts of shorter and/or longer carbon chains can also be present. If the carbon chain has no double bonds, it is a saturated oil, and is designated Cn:0 where n is the number of carbon atoms. Carbon chains with one double bond are monounsaturated and are designated Cn:1; those with two double bonds are designated Cn:2, and those with three double bonds are designated Cn:3. As examples, palmitic acid is a C16:0 acid, stearic acid is a C18:0 acid, oleic acid is a C18:1 acid, linoleic acid is a C18:2 acid, and linolenic acid is a C18:3 acid. The acids are in the combined state as triglycerides, and when the oils are hydrolyzed they are separated into the acid and glycerol components.

High oleic soybean oil has a C18:1 content of greater than 65% of the fatty acid moieties in the oil and a combined C18:2 and C18:3 content of less than 20% of the fatty acid moieties in the oil. In one embodiment, the HOS oil has a C18:1 content of greater than about 70% of the fatty acid moieties, and a combined C18:2 and C18:3 content of less than 15% of the fatty acid. In one embodiment, the HOS oil further comprises a combined C16:0 and C18:0 content of less than 15% of the fatty acid moieties. In one embodiment, the HOS oil has a C18:1 content of greater than about 75% of the fatty acid moieties, and a combined C18:2 and C18:3 content of less than 10% of the fatty acid moieties. In one embodiment, the HOS oil has a C18:1 content of greater than about 80% of the fatty acid moieties, and a combined C18:2 and C18:3 content of less than 10% of the fatty acid.

A mixture of polyol esters can be obtained in two synthesis steps from HOS oil. In the first synthesis step, the HOS oil comprising fatty acid moieties is converted to glycerol and a mixture of fatty acid esters through base-catalyzed reaction with an alcohol. The mixture of fatty acid esters comprises the fatty acid moieties of the HOS oil. The first synthetic step is represented in Scheme I below, where the alcohol is shown as $R^4OH$ and $R^1$, $R^2$, and $R^3$ represent the same or different $C_{15}$ to $C_{21}$ carbon chains of the fatty acid moieties in the triglyceride starting material and in the fatty acid ester products $R^1CO_2R^4$, $R^2CO_2R^4$, and $R^3CO_2R^4$. Note that in Scheme I only one triglyceride of the HOS oil is shown as the starting material, although the HOS oil contains a mixture of triglycerides such that the C16:0, C18:0, C18:1, C18:2, and C18:3 contents of the fatty acid moieties described in the embodiments of the high oleic soybean oil herein above are met.

Scheme 1

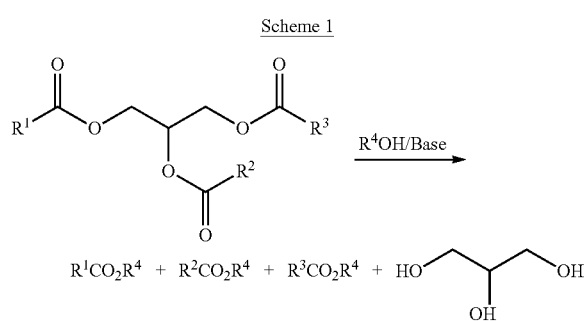

In the second synthesis step the mixture of fatty acid esters R¹CO₂R⁴, R²CO₂R⁴, and R³CO₂R⁴ is reacted with a polyol other than glycerol to produce a mixture of polyol esters, which comprises the fatty acid moieties of the HOS oil. The process for preparing a mixture of polyol esters can be performed as follows.

An HOS oil is reacted with an aliphatic monoalcohol having a chain length of from 1 to 5 carbons in the presence of a first base catalyst to produce a reaction mixture comprising glycerol and a mixture of the fatty acid esters corresponding to the fatty acid moieties of the HOS oil. In Scheme I the monoalcohol is shown as R⁴OH, where R⁴ represents an alkyl group containing from 1 to 5 carbons. This transesterification reaction can be driven to completion by (1) the use of excess monoalcohol (about 25 to 50 weight % based on HOS oil) and (2) separating and removing the glycerol that is formed during the transesterification of the fatty acid moieties of the HOS oil. Separation and removal of the glycerol also enables the ester mixture obtained in this step to be as free of any triglycerides of the HOS oil as possible. The glycerol may be separated, for example, by cooling the reaction mixture and allowing a bottom glycerol layer to form, due to glycerol having a higher density than the reaction mixture. Other conventional means of separation can be used such as liquid/liquid extraction, solvent extraction, salting out, or other separation methods that would not result in destruction of the esterified product. After separation the glycerol bottom layer can be physically removed by any conventional method known in the art.

The monoalcohol comprises methanol, ethanol, a propanol isomer, a butanol isomer, a pentanol isomer, or combinations thereof. In one embodiment, the monoalcohol comprises methanol. The first base catalyst can comprise sodium carbonate, potassium carbonate, lithium carbonate, sodium hydroxide, potassium hydroxide, lithium hydroxide, sodium methoxide, or combinations thereof. Other base catalysts known to one of ordinary skill can be used to obtain the same result, and any such catalyst can be useful in the practice of this invention. The amount of the first base catalyst used is typically from about 0.1 wt % to about 1.0 wt %, for example from about 0.1 wt % to about 0.5 wt %, based on the amount of HOS oil used. A larger amount of base can be used, but may not be necessary or economical. In one embodiment, the first base catalyst comprises sodium carbonate. In one embodiment, the first base catalyst comprises potassium carbonate. Transesterification of vegetable oil to the corresponding methyl esters is well-known and widely used to manufacture biodiesel, see for example [J. Braz. Chem. Soc., 1998, 9, 199-210].

Suitable reaction conditions for reacting HOS oil with an aliphatic monoalcohol include a reaction temperature from about 25° C. to about 150° C., for example from about 50° C. to about 100° C., and a reaction time from about 30 minutes to about 4 hours. In one embodiment, the reaction can be carried out under atmospheric pressure and refluxing conditions for about 3 or more hours.

In one embodiment, reacting the HOS oil with an aliphatic monoalcohol can be repeated more than once in a multi-stage process. The first stage is performed as described herein above. At the end of the first stage, the bottom layer of glycerol byproduct is separated and removed, more methanol and base catalyst are added to the mixture comprising triglycerides and fatty acid esters, and heating of the reaction mixture is continued to produce a second reaction mixture comprising glycerol and a mixture of fatty acid esters. The removal of glycerol, addition of more methanol and base, and heating steps are repeated until the triglycerides contained in the HOS oil have been transesterified to fatty acid esters. In one embodiment, the reaction of HOS oil with the aliphatic monoalcohol is performed in two stages. In a two stage process, a total about 30 weight % of the monoalcohol and a total of about 0.1 wt % to about 1.0 wt %, for example about 0.1 wt % to about 0.5 wt %, of the base catalyst are used, based on the amount of HOS oil used.

After removal of glycerol and excess aliphatic monoalcohol, the resulting mixture of fatty acid esters can be used in the next step of the process without further treatment. The yield of this transesterification reaction is almost quantitative. Optionally, however, the mixture of fatty acid esters obtained can have some remaining glycerol and/or glycerol esters (triglycerides). In one embodiment there is less than 10% of glycerol and/or glycerol esters present in the mixture. In another embodiment there is less than 5%, or less than 3%, or less than 1% of glycerol and/or glycerol esters in the fatty acid ester mixture. In one embodiment the mixture of fatty acid esters is essentially free of glycerol and/or glycerol esters. The composition of the fatty acid moieties in the mixture of fatty acid esters corresponds to the composition of the fatty acid moieties of the HOS oil.

The fatty acid esters are then reacted with a polyol in the presence of a second base catalyst to produce a reaction mixture comprising the aliphatic monoalcohol used in the first synthesis step and a mixture of polyol esters containing the fatty acid moieties of the HOS oil. The second base catalyst can be selected from the same group of catalysts as the first catalyst, and can be the same as the first catalyst or different from the first catalyst. The polyol comprises pentaerythritol, trimethylolpropane, neopentyl glycol, or combinations thereof. This transesterification reaction can be driven to higher conversion by the use of a slight excess of the fatty acid esters of the HOS oil, for example from about 1.15 to about 1.5 equivalents in relation to the total hydroxyl groups of the polyol, and by the removal of the monoalcohol formed during the transesterification with the polyol. Optionally, unreacted fatty acid esters can be removed by distillation.

In one embodiment, the polyol comprises pentaerythritol, and the second synthetic step can be represented as shown in Scheme II below, where R¹, R², R³, and R⁴ have the same meanings as defined above. Note that in Scheme II only three fatty acid esters of the starting mixture are shown, although the mixture contains a variety of fatty acid esters such that the C16:0, C18:0, C18:1, C18:2, and C18:3 contents of the fatty acid moieties of the HOS oil described herein above are met. Furthermore, only one generalized polyol ester product is shown, although a mixture of pentaerythritol esters comprising the fatty acid moieties of the HOS oil are produced and R can be R¹, R², and R³, or any combination.

Scheme II

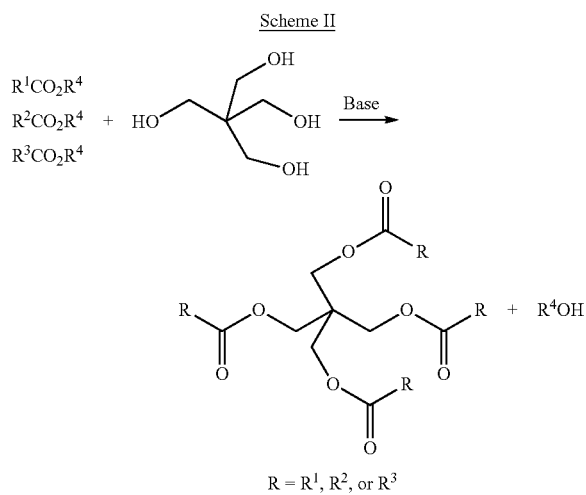

R = R¹, R², or R³

In one embodiment, the polyol comprises trimethylolpropane, and the second synthetic step can be represented as shown in Scheme III below, where $R^1$, $R^2$, $R^3$, and $R^4$ have the same meanings as defined above. Note that in Scheme III only three fatty acid esters of the starting mixture are shown, although the mixture contains a variety of fatty acid esters such that the C16:0, C18:0, C18:1, C18:2, and C18:3 contents of the fatty acid moieties of the HOS oil described herein above are met. Furthermore, only one generalized polyol ester product is shown, although a mixture of trimethylolpropane esters comprising the fatty acid moieties of the HOS oil are produced and R can be $R^1$, $R^2$, and $R^3$, or any combination.

Scheme III

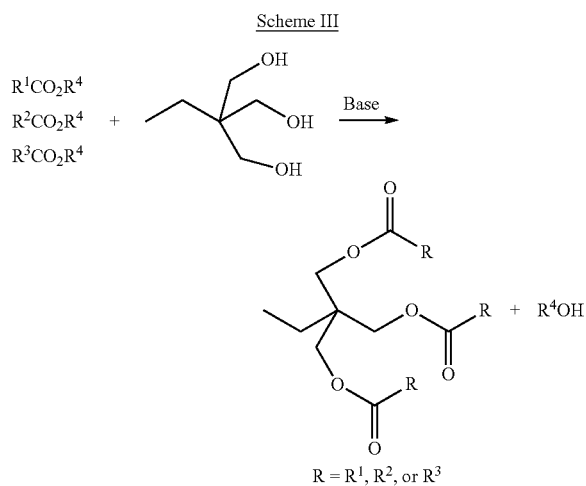

R = R¹, R², or R³

In one embodiment, the polyol comprises neopentyl glycol, and the second synthetic step can be represented as shown in Scheme IV below, where $R^1$, $R^2$, $R^3$, and $R^4$ have the same meanings as defined above. Note that in Scheme IV only three fatty acid esters of the starting mixture are shown, although the mixture contains a variety of fatty acid esters such that the C16:0, C18:0, C18:1, C18:2, and C18:3 contents of the fatty acid moieties of the HOS oil described herein above are met. Furthermore, only one generalized polyol ester product is shown, although a mixture of neopentyl glycol esters comprising the fatty acid moieties of the HOS oil are produced and R can be $R^1$, $R^2$, and $R^3$ or any combination.

Scheme IV

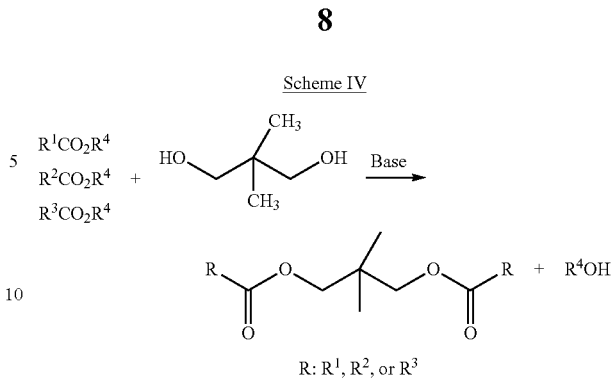

R: R¹, R², or R³

In any of the Schemes of the present invention the second base catalyst can be selected from the same group of catalysts as the first base catalyst, and can be the same as the first catalyst or different from the first catalyst. The second base catalyst can comprise sodium hydroxide, potassium hydroxide, lithium hydroxide, sodium methoxide, or combinations thereof, for example. In one embodiment, the second base catalyst comprises potassium hydroxide. Typically, the reaction temperature is slowly increased as the conversion to polyol esters proceeds, in order to avoid vigorous boiling of the monoalcohol byproduct and loss of the polyol while maintaining a high rate of reaction. The more volatile monoalcohol $R^4OH$ can be removed by distillation under reduced pressure. Suitable reaction conditions for reacting the fatty acid esters with the polyol include a reaction temperature from about 50° C. to about 200° C. and a reaction time from about 5 hours to about 150 hours under a vacuum in the range of 5 torr to about 100 torr. The preparation of pentaerythritol esters in high conversion may require higher temperature and longer reaction time.

After removal of the monoalcohol and optionally any unreacted fatty acid esters, the mixture of polyol esters can be separated from any higher-boiling by-products, for example by centrifuging the mixture and passing it through a thin layer of silica gel. The mixture of polyol esters can then be dried on full vacuum (0.5 torr or lower) at 110° C., typically for about 1 hour, to provide the final mixture of polyol esters.

Similarly, a mixture of polyol esters can be obtained from other vegetable oils, for example including but not limited to sunflower oil, canola oil, safflower oil, rapeseed oil, corn oil, olive oil, coconut oil, palm oil, castor oil, commodity soybean oil, high oleic sunflower oil, high oleic canola oil, and mixtures thereof. The characteristics of the mixture of polyol esters, for example the content of unsaturated and saturated moieties such as C18:1, C18:2, C13:3, C16:0, and C18:0 moieties, can reflect the composition of the vegetable oil(s) from which they are derived. Optionally, a mixture of polyol esters can be refined, for example by distillation, to separate one or more polyol esters from the mixture, or to enrich or deplete the mixture with respect to one or more of the polyol esters. In one embodiment of the process for preparing a mixture of polyol esters, the process further comprises providing at least one vegetable oil other than high oleic soybean oil in addition to the high oleic soybean oil.

IMC-130 Canola oil, available from Cargill, Inc., has an oleic acid content of about 75% and a polyunsaturated fatty acid content (C18:2 and C18:3) of about 14%. U.S. Pat. No. 5,767,338 describes plants and seeds of IMC-130. See also U.S. Pat. No. 5,861,187. High oleic sunflower oils having oleic acid contents, for example, of about 77% to about 81%, or about 86% to about 92%, can be obtained from A. C.

Humko, Memphis Tenn. U.S. Pat. No. 4,627,192 describes high oleic acid sunflower oils.

The mixture of polyol esters derived from reaction of a polyol comprising pentaerythritol, trimethylolpropane, neopentyl glycol, or combinations thereof and a mixture of fatty acid esters derived from HOS oil can be used as a dielectric fluid. In preferred embodiments, the dielectric fluid comprises at least about 30 wt %, or at least about 50 wt %, or at least about 70 weight percent, or at least about 80 wt %, or at least about 90 wt % to about 100 wt %, of the mixture of polyol esters comprising the fatty acid moieties of the HOS oil. The dielectric fluid may further comprise from about 1 wt % to about 70 wt %, for example from about 1 wt % to about 50 wt %, or from about 1 wt % to about 30 wt %, or from about 1 wt % to about 20 wt %, or from about 1 wt % to about 10 wt % of a blending component comprising other dielectric fluids such as vegetable oils, vegetable oil based fluids, algal oils, one or more polyol esters derived from a vegetable oil other than HOS oil, mineral oils, synthetic esters, silicon fluids, poly alpha olefins, or mixtures thereof based on the total weight of the dielectric fluid. In one embodiment, the dielectric fluid further comprises a blending component selected from the group consisting of vegetable oil, algal oil, one or more polyol esters derived from a vegetable oil other than HOS oil, mineral oil, silicone fluids, synthetic esters, poly alpha olefins, or mixtures thereof. Examples of vegetable oil based fluids that can be used are Envirotemp® FR3™ fluid (Cooper Industries, Inc.) and BIOTEMP® Biodegradable Dielectric Insulating Fluid (ABB). The term "algal oil" refers to the lipid components, including triacylglycerols, produced by microalgal cells such as *Chlorella, Parachlorella, Dunaliella*, and others, for example as disclosed in published patent application US 2010/0303957. An example of a high fire point hydrocarbon oil that can be used is R-Temp® hydrocarbon oil (Cooper Industries, Inc.). Examples of synthetic esters include polyol esters which contain fatty acid moieties of less than about 10 carbon atoms in chain length. Commercially available synthetic esters that can be used include those sold under the trade names Midel® 7131 (The Micanite and Insulators Co., Manchester UK), REOLEC® 138 fluid (FMC, Manchester, UK), and ENVIROTEMP 200 fire-resistant fluid (Cooper Power Fluid Systems).

The dielectric fluids can contain other useful additives, for example oxidation inhibitors, metal deactivators, in particular copper deactivators, corrosion inhibitors, flame retardants, thermal stabilizers, viscosity modifiers, pour point depressants, anti-foaming agents, acid-base indicators, and dyes, provided that the additives are soluble in the compositions, are thermally stable at high temperatures, and do not deleteriously affect the electrical properties of the dielectric fluid. In one embodiment, the dielectric fluid further comprises at least one additive selected from the group consisting of oxidation inhibitors, corrosion inhibitors, metal deactivators, and pour point depressants.

Among the properties that are desirable for useful and efficient dielectric fluids are high dielectric breakdown voltage, low dissipation factor, high specific heat, high thermal conductivity, low coefficient of expansion, low viscosity, low sensitivity of viscosity to temperature, low pour point temperatures, low volatility, high flash point, and low moisture content. The dielectric fluids of the present invention possess a wide variety of these desirable properties, as well as good oxidative stability. Oxidative stability is related to the degree of unsaturation in the dielectric fluid and can be measured, for example by using a standard method for determining an oil stability index. The high oleic acid content of the soybean oil used to prepare polyol esters of the present invention helps to provide good oxidative stability to the disclosed dielectric fluids. In addition, the dielectric fluids disclosed herein are expected to be biodegradable as they are derived from a vegetable oil which is readily biodegradable. A dielectric fluid comprising a mixture of TMP esters derived from the fatty acids of crude HOS oil has been found to meet the criteria for "Ready Biodegradation" under the conditions of the 28-day $CO_2$ Evolution test according to OECD Guideline 301B. Published Canadian Patent Application CA 2594765 discloses a biodegradability (28 d BOD/COD) of 72% for the trioleate ester of trimethylolpropane. The dielectric fluids disclosed herein are suitable for use in any application requiring electrical insulation fluids having the properties of the fluids disclosed herein, such as liquid-filled power transformers, distribution transformers, traction transformers, reactors, and their accessory equipment such as switches and tap changers, all of which are fluid-filled. The combination of fluid and solid insulation such as kraft paper, kraft board, aramid paper, cotton paper, aramid board, or composites (i.e., fiber glass/epoxy, nylon, polyester), provides electrical insulation for the electrical apparatus. In addition, the fluid serves as a heat transfer medium to aid in cooling electrical devices. In one embodiment, the electrical apparatus comprising the dielectric fluid disclosed herein is an electrical transformer, an electrical capacitor, a fluid-filled transmission line, an electrical power cable, an electrical inductor, or a high voltage switch.

In one embodiment, a dielectric material is impregnated with at least 10 weight percent of a dielectric fluid, wherein the dielectric material comprises a cellulosic paper, a synthetic paper, or a nonwoven web; and the dielectric fluid comprises a cellulosic paper, a synthetic paper, or a nonwoven web; and the dielectric fluid comprises a mixture comprising polyol esters derived from a reaction of: a) a polyol comprising pentaerythritol, trimethylolpropane, neopentyl glycol, or combinations thereof; and b) a mixture of fatty acid esters derived from a high oleic soybean oil comprising fatty acid moieties, wherein the high oleic soybean oil has i) a C18:1 content of greater than 65% of the fatty acid moieties in the oil; and ii) a combined C18:2 and C18:3 content of less than 20% of the fatty acid moieties in the oil. The dielectric material can be impregnated with at least about 5 weight percent, or at least about 10 weight percent, or at least about 15 weight percent, or at least about 20 weight percent of a dielectric fluid. The dielectric material can be impregnated with the dielectric fluid such that it is saturated with the dielectric fluid. The term "synthetic paper" as used herein refers to any non-cellulose or cloth paper, for example an aramid-based paper.

The dielectric fluids disclosed herein provide new alternatives to mineral oil and petroleum-based synthetic esters containing fatty acid moieties of less than about 10 carbon atoms in chain length—alternatives which are derived from a renewable starting material, high oleic soybean oil, and which have desired properties, including a high fire point and a low pour point. They also provide superior low temperature performance over vegetable oil-based fluids. In one embodiment, the dielectric fluid comprising a mixture of polyol esters has a flash point of greater than about 280° C. In one embodiment, the dielectric fluid has a flash point of greater than about 310° C. In one embodiment, the dielectric fluid has a flash point of greater than about 320° C. In one embodiment, the dielectric fluid has a pour point of less than about −10° C. In one embodiment, the dielectric fluid has a pour point of less than about −30° C. In one embodiment, the dielectric fluid has a flash point of greater than about 280° C. and a pour point of less than about −10° C. In one embodiment, the dielectric fluid has a fire point of greater than about 325° C. In one embodiment, the dielectric fluid has a fire point of greater than about 370° C. In one embodiment, the dielectric fluid has a fire point of greater than about 325° C. and a pour point of less than about −10° C. In one embodiment, the dielectric fluid has a fire point of greater than about 325° C. and a pour point of less than about −30° C. In one embodiment, the dielectric fluid has a viscosity of less than about 45 cST at 40° C. and less than about 14 cST at 100° C. In one embodiment, the dielectric fluid has a viscosity of less than about 25 cST at 40° C. and less than about 10 cST at 100° C. In one embodiment, the dielectric fluid has a power factor of less than about 0.15% at 25° C. and less than about 5% at 100° C. In one embodiment, the dielectric fluid has a power factor of less than about 0.03% at 25° C. and less than about 3% at 100° C. In one embodiment, the dielectric fluid has a dielectric breakdown voltage of greater than about 35 KV when measured across a 1 mm gap at 25° C. In one embodiment, the dielectric fluid has an oil stability index of at least about 8 hours at 110° C. In one embodiment, the dielectric fluid has an oil stability index of at least about 14 hours at 110° C. In one embodiment, the dielectric fluid has an oil stability index of at least about 25 hours at 110° C.

Also disclosed herein is a method of using an electrical apparatus, the method comprising employing in the apparatus a dielectric fluid comprising a mixture comprising polyol esters derived from a reaction of a) a polyol comprising pentaerythritol, trimethylolpropane, neopentyl glycol, or combinations thereof, and b) a mixture of fatty acid esters derived from a high oleic soybean oil comprising fatty acid moieties, wherein the high oleic soybean oil has i) a C18:1 content of greater than 65% of the fatty acid moieties in the oil, and ii) a combined C18:2 and C18:3 content of less than 20% of the fatty acid moieties in the oil.

The dielectric fluids disclosed herein may be used to retrofill existing electrical equipment that incorporates other, less desirable dielectric fluids. These other fluids may be replaced with dielectric fluid comprising a mixture of polyol esters as disclosed herein using any suitable method known in the art.

EXAMPLES

The methods described herein are illustrated in the following examples. From the above discussion and these examples, one skilled in the art can ascertain the essential characteristics of this invention, and without departing from the spirit and scope thereof, can make various changes and modifications of the invention to adapt it to various uses and conditions.

The following materials were used in the examples. All commercial reagents were used as received. The silica gel was dried in a vacuum oven at 200° C. for 3 days under about 200 torr vacuum before use.

Refined, bleached, and deodorized high oleic soybean oil (RBD HOS oil) containing triglycerides of the following fatty acids: palmitic acid (6.5 wt %), stearic acid (4.15 wt %), oleic acid (73.9 wt %), linoleic acid (8.77 wt %), and linolenic acid (2.94 wt %) was obtained according to U.S. Pat. No. 5,981,781. Crude high oleic soybean oil (HOS oil) containing palmitic acid (6.5 wt %), stearic acid (4.1 wt %), oleic acid (74.8 wt %), linoleic acid (7.6 wt %), and linolenic acid (2.8 wt %) was obtained according to U.S. Pat. No. 5,981,781. Commodity Market Pantry™ brand name soybean oil containing triglycerides of the following fatty acids: palmitic acid (10.3 wt %), stearic acid (4.6 wt %), oleic acid (22.7 wt %), linoleic acid (53.5 wt %), and linolenic acid (7.2 wt %) was purchased from a Target store.

Methanol (99.8%), sodium carbonate (99.5%), potassium hydroxide (>85%), hexanes (99.9%), silica gel 60 and potassium carbonate (99.9%) were obtained from EMD Chemicals Inc. (Gibbstown, N.J.). Neopentyl glycol (99%), trimethylolpropane (97%), and pentaerythritol (98%) were obtained from Aldrich Company (Milwaukee, Wis.).

The following abbreviations are used: "GC" is gas chromatography, "C" is Celsius, "mm" is millimeter, "mL" is milliliter, "L" is liter, "min" is minute, "cm" is centimeter, "g" is gram(s), "mg" is milligrams, "h" is hour(s), "temp" or "T" is temperature, "Comp. Ex." Is Comparative Example, "ID" is internal diameter, "NPG" is neopentyl glycol, "TMP" is trimethylolpropane, and "PE" is pentaerythritol. "ASTM" stands for American Society for Testing and Materials which provides standard protocols for material evaluation. "AOCS" stands for American Oil Chemists' Society which provides standard methods for material evaluation. "OECD" stands for Organization for Economic Co-operation and Development.

Methyl esters were analyzed using an Agilent 6890 Series GC with a Omegawax™ 320 column, 30 m long, diameter 320 µm, film thickness 0.30 µm. Oven ramp: Initial temp 160° C. holds for 5 minutes, then increase at 2° C./min to 220° C. and hold for 10 minutes, then increase at 20° C./min to 240° C. and hold for 5 minutes. The carrier gas was helium. Injection port 250° C., with pressure 11.55 psi; split ratio 50:1 split flow: 77.8 mL/min; total flow: 82.3 mL/min. Initial flow rate 1.6 ml/min with 11.56 psi. Flame ionization detector used set at 270° C., hydrogen flow 35 mL/min; air flow 400 mL/min; Mode constant column+makeup flow; combined flow 32.0, make up gas was helium. Reference standard GLC-461 (a mixture of 32 different methyl esters C4:0 to C24:1) from Nu-Chek Prep, INC. (Elysian, Minn.) was used to identify retention times of the methyl esters.

The properties of the polyol ester mixtures were evaluated according to the following test methods:

TABLE 1

Properties Measured and Test Methods Used

| Property | Test Method |
| --- | --- |
| Flash point | ASTM D-92 |
| Fire point | ASTM D-92 |
| Pour point | ASTM D-97 |
| Moisture in oil | ASTM D-1533 |
| Acid number | ASTM D-974 |
| Dielectric Breakdown Voltage | ASTM D-1816 |
| Power factor | ASTM D-924 |
| Resistivity | ASTM D-1169 |
| Viscosity | ASTM D-445 or obtained by using a TR 2000 rotational rheometer with a 28 mm DIN concentric cylinder geometry |
| Oil stability index | AOCS Cd 12b-92 (1997) |

Example 1

Preparation of a Mixture of Methyl Esters Comprising the Fatty Acid Moieties of RBD HOS Oil A 2-L flask equipped with an overhead stirrer, condenser, and nitrogen blanket was charged with RBD HOS Oil (1007 g), methanol (249 g), and sodium carbonate (2 g). The reaction mixture was heated to reflux for 6.5 hours (final temperature was about 76° C.) while stirring at 360 rpm. After being cooled to room temperature, the reaction mixture was transferred into a separatory funnel and allowed to sit overnight at room temperature. The resulting bottom layer containing glycerol (170 g) was removed. The top layer was distilled under reduced pressure (1 torr) at 60° C. for 40 minutes to remove the remaining methanol (56.7 g). After removal of an additional glycerol layer (~1 g) in a separatory funnel, the mixture of methyl esters (1006 g) was obtained as the remainder. GC analysis indicated it contained methyl palmitate (6.4 wt %), methyl stearate (4.0 wt %), methyl oleate (73.6 wt %), methyl linoleate (8.6 wt %), and methyl linolenate (2.7 wt %).

Example 2

Preparation of a Mixture of Methyl Esters Comprising the Fatty Acid Moieties of Crude HOS Oil A 20-liter, jacketed, Pyrex® reactor equipped with mechanical stirring, reflux condenser, internal thermocouple, nitrogen inlet, and a drain was dried by sweeping with nitrogen overnight. The reactor was charged with crude HOS oil (12.0 kg), methanol (3.0 kg) and potassium carbonate (45 g). The mixture was heated to reflux under nitrogen for 3 hours. The reaction mixture was cooled to 25° C. The bottom layer containing glycerol (1.9 kg) was removed via the drain. The reactor, containing the top layer, was charged with methanol (400 g) and potassium carbonate (2.0 g). The mixture was heated to reflux for 2 hours. After being cooled to room temperature, the top layer of the reaction mixture was transferred to a 22-liter RB flask. The remaining methanol was distilled off at 50° C. under vacuum (200 to 5 torr) to give 11.48 kg of a mixture of crude methyl esters. GC analysis indicated that it contained methyl palmitate (6.5 wt %), methyl stearate (3.9 wt %), methyl oleate (76.1 wt %), methyl linoleate (7.0 wt %), and methyl linolenate (2.8 wt %).

Example 3

Preparation of a Mixture of NPG Esters from a Mixture of Methyl Esters Comprising the Fatty Acid Moieties of RBD HOS Oil A mixture of the methyl esters comprising the fatty acid moieties of RBD HOS oil from Example 1 (917 g), KOH (2.0 g), and neopentyl glycol (139 g) was heated under 2 torr vacuum to 40-50° C. for 3 hours, then 50-100° C. for 1 hour, then 100-160° C. for 3 hours. During the heating period, the temperature gradually increased while the boiling slowed down. A total about 86.2 g of MeOH was recovered during the reaction in a liquid nitrogen trap. The reaction mixture was distilled under 30 m torr vacuum up to 210° C. to recover the unreacted methyl esters as distillate (95 g). The distillation residue was centrifuged and the resulting liquid was passed through a silica gel column [2" (OD)×4"] to give a mixture of NPG esters as the product (732.6 g). The solid from the centrifuge was extracted with hexanes (2×150 mL). The silica gel column was washed with the combined hexane extracts and additional hexanes (300 mL). The combined hexane washes were concentrated and dried under vacuum to give an additional amount of the NPG esters as product (93.5 g). $^1$H NMR analysis of the product confirmed its identify as a mixture of esters comprising neopentyl glycol and fatty acid moieties of RBD HOS oil. The composition was found to comprise 1% NPG monoesters, 97% NPG diesters, and 2% triglycerides (HOS oil).

Example 4

Preparation of a Mixture of NPG Esters from a Mixture of Methyl Esters Comprising the Fatty Acid Moieties of Crude HOS Oil A mixture of the methyl esters comprising the fatty acid moieties of crude HOS oil from Example 2 (1196 g), KOH (2.38 g), and neopentyl glycol (178 g) was heated under 30-5 torr vacuum to 50-205° C. for 14 hours. The unreacted methyl esters (163 g) were recovered by reduced pressure distillation at about 15 mTorr. The distillation residue was centrifuged and the resulting liquid was passed through a silica gel column (22 g silica gel) to give a mixture of NPG esters as the product (910 g) after being dried at 110° C. under 20 m Torr vacuum for 1 hour. The solid from the centrifuge was extracted with hexanes (2×150 mL). The silica gel column was washed with the combined hexane extracts and additional hexanes (300 mL). The combined hexane washes were concentrated and dried under vacuum to give an additional amount of the NPG esters product (170 g). $^1$H NMR analysis of the product confirmed its identify as a mixture of esters comprising neopentyl glycol and fatty acid moieties of crude HOS oil. The composition was found to comprise 2% NPG monoesters, 93% NPG diesters, and 5% triglycerides (HOS oil).

The suitability of using the product as a dielectric fluid was evaluated by measuring its electrical and physical properties using the methods listed in Table 1. Results are given in Table 2.

Example 5

Preparation of a Mixture of TMP Esters from a Mixture of Methyl Esters Comprising the Fatty Acid Moieties of RBD HOS Oil A mixture of the methyl esters comprising the fatty acid moieties of RBD HOS oil from Example 1 (1094 g), KOH (2.2 g), and trimethylolpropane (140 g) was heated under 10 torr to 95° C. over 6 hours, then to 154° C. over an additional 4.5 hours. Additional KOH (0.47 g) was added and the mixture was heated under 0.8 torr at 123-150° C. for 8 hours more. During the heating period, the temperature gradually increased while the boiling slowed down. A total about 86.2 g of MeOH was recovered from the liquid nitrogen trap. The reaction mixture was distilled under 45 m torr vacuum up to 239° C. The unreacted methyl esters were collected as distillate (57.8 g). The distillation residue was centrifuged and the resulting liquid was passed through a silica gel column (~14 g) to give a mixture of TMP esters as the product (970 g). The solid from the centrifuge was extracted with hexanes. The silica gel column was washed with the combined hexane extracts and additional hexanes (300 mL). The combined hexane washes were concentrated and dried under vacuum to give an additional amount of the mixture of TMP esters product (75 g).

A portion of the product obtained (847 g) was mixed with bleaching clay grade F-115FF (from BASF, 8.8 g), and Celite (2.2 g), and stirred at room temperature under vacuum (1 torr) for 1 hour, then heated to 110° C. for 1 hour under 0.5 torr. The mixture was cooled to room temperature and passed through a ½" silica gel column (ID 1.5"). The collected product was heated to 110° C. for 1 hour under 0.1 torr before it was evaluated. $^1$H NMR analysis of the product confirmed its identify as a mixture of esters comprising trimethylolpropane and fatty acid moieties of RBD HOS oil. The composition was found to comprise 2% TMP diesters, 90% TMP triesters, and 8% triglycerides (HOS oil).

The suitability of using the product as a dielectric fluid was evaluated by measuring its electrical and physical properties using the methods listed in Table 1. Results are given in Table 2.

Example 6

Preparation of a Mixture of TMP Esters from a Mixture of Methyl Esters Comprising the Fatty Acid Moieties of Crude HOS Oil A mixture of the methyl esters comprising the fatty acid moieties of crude HOS oil from Example 2 (1213 g), KOH (2.4 g), and trimethylolpropane (156 g) was heated under 10 torr to 103° C. over 2 hours. Then the pressure was reduced to 15 torr and the reaction mixture was heated to 193° C. over 7.5 hour. The reaction mixture was then distilled under 40 mTorr vacuum to recover the unreacted methyl esters as distillate. The distillation residue was centrifuged and the resulting liquid was passed through a silica gel column (18 g silica gel) to give an oil which was further dried under 30 mTorr at 110° C. for 1 hour to give a mixture of TMP esters as the product (962 g). The solid from the centrifuge was extracted with hexanes. The silica gel column was washed with the combined hexane extracts and additional hexanes. The combined hexane washes were concentrated and dried to give an additional amount of product (108 g). $^1$H NMR analysis of the product confirmed its identify as a mixture of esters comprising trimethylolpropane and fatty acid moieties of crude HOS oil. The composition was found to comprise 1.4% TMP diesters, 97.4% TMP triesters, and 1.2% triglycerides (HOS oil).

The suitability of using the product as a dielectric fluid was evaluated by measuring its electrical and physical properties using the methods listed in Table 1. Results are given in Table 2.

For biodegradability testing, another sample of the mixture of TMP esters was prepared from a mixture of methyl esters comprising the fatty acid moieties of crude HOS oil. The sample was prepared similarly to the TMP ester mixture of Example 6, and its composition was found by $^1$H NMR analysis to comprise 90.2% TMP triesters, 2% TMP diesters, and 7.8% triglycerides (HOS oil).

Ready biodegradability of the TMP ester mixture was evaluated using the 28-day $CO_2$ Evolution Test for "Ready Biodegradation" according to the OECD Guideline 301B in the version dated Jul. 17, 1992. The biological system used was secondary activated sludge from the Elkton, Md. (USA) Publicly-Owned Treatment Works. The TMP ester mixture was found to meet the criteria for "Ready Biodegradation" under the conditions of the test. The test material reached a maximum biodegradability of 74%. Greater than 60% biodegradability was reached within 10 days of exceeding 10% biodegradation.

Example 7

Preparation of a Mixture of PE Esters from a Mixture of Methyl Esters Comprising the Fatty Acid Moieties of RBD HOS Oil A mixture of the methyl esters comprising the fatty acid moieties of RBD HOS oil from Example 1 (100.6 g), KOH (0.2 g), and pentaerythritol (9.8 g) was heated under 5 torr to 80° C. over 1.5 hours and held at 80° C. for 1.5 hours, then heated to 160° C. over 4.5 hours. The reaction mixture was then distilled under 18 m torr vacuum to recover the unreacted methyl esters as distillate. The distillation residue was centrifuged and the resulting liquid was passed through a short silica gel column to give a mixture of PE esters as the product (60.4 g). The solid from the centrifuge was extracted with hexanes. The silica gel column was washed with the combined hexane extracts and additional hexanes. The combined hexane washes were concentrated and dried to give an additional amount of the mixture of PE esters product (21.6 g). $^1$H NMR analysis of the product confirmed its identify as a mixture of esters comprising pentaerythritol and fatty acid moieties of RBD HOS oil. The composition was found to comprise 1.5% PE triesters, 94% PE tetraesters, and 4.5% triglycerides (HOS oil).

Example 8

Preparation of a Mixture of PE Esters from a Mixture of Methyl Esters Comprising the Fatty Acid Moieties of Crude HOS Oil A mixture of the methyl esters comprising the fatty acid moieties of crude HOS oil from Example 2 (1190 g), KOH (2.41 g), and pentaerythritol (116 g) was heated under 1-100 torr at 80-205° C. for 65 hours. More KOH (1.3 g) was added and the reaction mixture was further heated under 5 torr at 200-220° C. for 34 hours. The excess methyl esters were removed by distillation under 1 torr vacuum at 235-330° C. pot temperature. The distillation residue was centrifuged and the resulting liquid was passed through a silica gel column (14 g), then dried at 110° C. under 0.1 torr vacuum for 1 hour to give a mixture of PE esters as the product (930 g). $^1$H NMR analysis of the product confirmed its identify as a mixture of esters comprising pentaerythritol and fatty acid moieties of crude HOS oil. The composition was found to comprise 4% PE triesters, 90% PE tetraesters, and 6% triglycerides (HOS oil).

The suitability of using the product as a dielectric fluid was evaluated by measuring its electrical and physical properties using the methods listed in Table 1. Results are given in Table 2.

Comparative Example A

Preparation of a Mixture of Methyl Esters Comprising the Fatty Acid Moieties of Commodity Soybean Oil A 2-L flask equipped with an overhead stirrer, condenser, and nitrogen blanket was charged with Market Pantry™ brand name soybean oil (1009 g), methanol (250 g), and potassium carbonate (3.1 g). The reaction mixture was heated to reflux for 3.5 hours. The resulting bottom layer containing glycerol was removed, and more methanol (50 g) and potassium carbonate (0.2 g) were added. The reaction mixture was refluxed for another 3.5 hours. After the reaction mixture was cooled to room temperature, the excess methanol was removed by vacuum distillation at 25° C. for 1 hour. The product layer was filtered through a thin layer of silica to give a mixture of methyl esters comprising the fatty acid moieties of commodity soybean oil (968 g).

Comparative Example B

Preparation of a Mixture of TMP Esters from a Mixture of Methyl Esters Comprising the Fatty Acid Moieties of Commodity Soybean Oil A mixture of the methyl esters comprising the fatty acid moieties of commodity soybean oil from Comparative Example A (968 g), trimethylolpropane (97.9 g), and sodium methoxide (1.8 g) was heated to 68° C. in 1 hour under 5-Torr vacuum. The reaction temperature was then slowly increased to 185° C. over 6 hours. The excess methyl esters were removed by distillation under vacuum (~20-m torr) at 225° C. pot temperature. The distillation residue was centrifuged and the resulting liquid was passed through a silica gel column (14 g) then dried at 110° C. under 0.1 Torr vacuum for 1 hour to give a mixture of TMP esters as the product (597 g). $^1$H NMR analysis of the product confirmed its identity as a mixture of esters comprising trimethylolpropane and fatty acid moieties of commodity soybean oil.

The suitability of using the product as a dielectric fluid was evaluated by measuring its electrical and physical properties using the methods listed in Table 1. Results are given in Table 2.

The polyol ester mixtures obtained in Example 4, Example 5, Example 6, Example 8, and Comparative Example B were evaluated using the methods listed in Table 1. Samples of Envirotemp® FR3™ fluid (Cooper Industries, Inc.), which is a vegetable oil-based fluid formulated from commodity soybean oil, and Midel® 7131 (The Micanite and Insulators Co., Manchester UK), which is a synthetic ester composition of linear and branched $C_5$ to $C_{10}$ fatty acids as mixed esters with pentaerythritol, were also evaluated using the same methods. The data are presented in Table 2.

7131 fluids contain added antioxidants the more meaningful comparison is between the dielectric fluids of Examples 4 though 8 and Comparative Example B as these materials did not contain added antioxidants. The fluids of Examples 4 through 8 demonstrated significantly longer induction periods than did that of Comparative Example B, reflecting the greater oxidative stability provided by the higher content of unsaturated moieties.

What is claimed is:

1. A dielectric fluid comprising:
   a mixture comprising polyol esters derived from a reaction of:
   a) a polyol comprising pentaerythritol, trimethylolpropane, neopentyl glycol, or combinations thereof; and
   b) a mixture of fatty acid esters derived from a high oleic soybean oil comprising fatty acid moieties, wherein the high oleic soybean oil has
      i) a C18:1 content of greater than 65% of the fatty acid moieties in the oil; and
      ii) a combined C18:2 and C18:3 content of less than 20% of the fatty acid moieties in the oil.

2. The dielectric fluid of claim 1, wherein the dielectric fluid has a flash point of greater than about 280° C.

3. The dielectric fluid of claim 2, wherein the dielectric fluid has a pour point of less than about −10° C.

TABLE 2

Summary of Dielectric Fluid Properties Measured

| Properties Measured | Envirotemp® FR3 ™ | Midel® 7131 | Example 4 | Example 5 | Example 6 | Example 8 | Comp. Ex. B |
|---|---|---|---|---|---|---|---|
| Flash point (° c.) | 328 | 263 | 288 | 318 | 324 | 338 | 320 |
| Fire point (° c.) | 352 | 306 | 330 | 374 | 378 | 378 | 382 |
| Pour point (° c.) | −20 | −50 | −14 | −38 | −38 | −14 | −41 |
| H$_2$O (ppm) | 281 | 77 | 43 | 25 | 23 | 19 | 18 |
| Power Factor (%) 25° C. | 0.164 | 0.023 | 0.132 | 0.022 | 0.023 | 0.149 | 2.02 |
| Power Factor (%) 100° C. | 3.01 | 0.75 | 4.8 | 0.9 | 0.81 | 2.98 | 19.6 |
| Dielectric Breakdown Voltage (KV) (1 mm gap @25° C.) | 30 | 43 | 36 | 45 | 39 | 48 | not measured |
| Resistivity (E12 ohm-cm) | 5.65 | 0.231 | 10.9 | 6.02 | 4.64 | 12.4 | 1.59 |
| Acid Number (mg KOH/g) | 0.037 | 0.03 | 0.165 | 0.015 | 0.007 | 0.516 | 0.022 |
| Viscosity (cST) 40° C. | 34 | 28* | 24 | 41.8* | 41.8* | 23.6 | 36 |
| Viscosity (cST) 100° C. | 8 | 5* | 6 | 9* | 9* | 13.6 | 8.4 |
| OSI (hours at 110° C.) | 9.7 | >100 | 28.2 | 14 | 8.5 | 26 | 1.4 |

*Measured by a TR 2000 rotational rheometer

The data in Table 2 show that the mixtures of polyol esters of the Examples have desirable properties for use as dielectric fluids. The flash points and fire points of the fluids of the Examples are suitably high, and significantly higher than those of the synthetic ester composition Midel® 7131. They also have significantly lower moisture content than Midel® 7131 and the vegetable oil-based Envirotemp® FR3™. In comparison to the polyol esters of Comparative Example B (derived from the reaction of trimethylolpropane and the mixture of methyl esters of fatty acid moieties derived from commodity soybean oil), the analogous polyol esters of Example 5 (derived from the reaction of trimethylolpropane and the mixture of methyl esters of fatty acid moieties derived from high oleic soybean oil) show better electrical properties in terms of the power factor, both when measured at 25° C. and when measured at 100° C. The extremely high power factors of the fluid of Comparative Example B would preclude its use as a dielectric fluid. In contrast, the characteristics of the fluid of Example 5 show that it is suitable for use as a dielectric fluid. In terms of OSI values, which reflect oxidative stability, as both Envirotemp® FR3™ and Midel®

4. The dielectric fluid of claim 1, wherein the dielectric fluid has a viscosity of less than about 45 cST at 40° C. and less than about 14 cST at 100° C.

5. The dielectric fluid of claim 1, wherein the dielectric fluid has a power factor of less than about 0.15% at 25° C. and less than about 5% at 100° C.

6. The dielectric fluid of claim 1, wherein the dielectric fluid has a dielectric breakdown voltage of greater than about 35 KV when measured across a 1 mm gap at 25° C.

7. The dielectric fluid of claim 1, wherein the dielectric fluid has an oil stability index of at least about 8 hours at 110° C.

8. The dielectric fluid of claim 1, further comprising at least one additive selected from the group consisting of oxidation inhibitors, corrosion inhibitors, metal deactivators, and pour point depressants.

9. The dielectric fluid of claim 1, further comprising a blending component selected from the group consisting of vegetable oil, algal oil, one or more polyol esters derived from a vegetable oil other than high oleic soybean oil, mineral oil, silicone fluids, synthetic esters, poly alpha olefins, or mixtures thereof.

10. The dielectric fluid of claim 1, wherein the polyol comprises pentaerythritol.

11. The dielectric fluid of claim 1, wherein the polyol comprises trimethylolpropane.

12. The dielectric fluid of claim 1, wherein the polyol comprises neopentyl glycol.

13. The dielectric fluid of claim 1, wherein the C18:1 content is greater than 70% of the fatty acid moieties in the oil, and the combined C18:2 and C18:3 content is less than 15% of the fatty acid moieties in the oil.

14. The dielectric fluid of claim 1, wherein the dielectric fluid meets the criteria for "Ready Biodegradation" under the conditions of the 28-day $CO_2$ Evolution Test according to OECD Guideline 301B.

15. A process for preparing a mixture of polyol esters, the process comprising the steps of:
   a) providing a high oleic soybean oil comprising fatty acid moieties wherein the soybean oil comprises
      i) a C18:1 content of greater than 65% of the fatty acid moieties in the oil; and
      ii) a combined C18:2 and C18:3 content of less than 20% of the fatty acid moieties in the oil;
   b) reacting the high oleic soybean oil with an aliphatic monoalcohol having a chain length of from 1 to 5 carbons in the presence of a first base catalyst to produce a reaction mixture comprising glycerol and a mixture of fatty acid esters;
   c) separating and removing the glycerol; and
   d) reacting the mixture of fatty acid esters with a polyol comprising pentaerythritol, trimethylolpropane, neopentyl glycol, or combinations thereof in the presence of a second base catalyst to produce a mixture of polyol esters.

16. An electrical apparatus comprising:
a dielectric fluid wherein the dielectric fluid comprises a mixture comprising polyol esters derived from a reaction of:
   a) a polyol comprising pentaerythritol, trimethylolpropane, neopentyl glycol, or combinations thereof; and
   b) a mixture of fatty acid esters derived from a high oleic soybean oil comprising fatty acid moieties, wherein the high oleic soybean oil has
      i) a C18:1 content of greater than 65% of the fatty acid moieties in the oil; and
      ii) a combined C18:2 and C18:3 content of less than 20% of the fatty acid moieties in the oil.

17. The electrical apparatus of claim 16, wherein the electrical apparatus is an electrical transformer, an electrical capacitor, a fluid-filled transmission line, an electrical power cable, an electrical inductor, or a high voltage switch.

18. A dielectric material impregnated with at least 10 weight percent of a dielectric fluid, wherein the dielectric material comprises a cellulosic paper, a synthetic paper, or a nonwoven web; and the dielectric fluid comprises a mixture comprising polyol esters derived from a reaction of:
   a) a polyol comprising pentaerythritol, trimethylolpropane, neopentyl glycol, or combinations thereof; and
   b) a mixture of fatty acid esters derived from a high oleic soybean oil comprising fatty acid moieties, wherein the high oleic soybean oil has
      i) a C18:1 content of greater than 65% of the fatty acid moieties in the oil; and
      ii) a combined C18:2 and C18:3 content of less than 20% of the fatty acid moieties in the oil.

* * * * *